US009192499B2

(12) United States Patent
Gibbons, Jr.

(10) Patent No.: US 9,192,499 B2
(45) Date of Patent: Nov. 24, 2015

(54) INNER CATHETER FOR A SELF-EXPANDING MEDICAL DEVICE DELIVERY SYSTEM WITH A CLOSED COIL WIRE

(71) Applicant: Cook Medical Technologies LLC, Bloomington, IN (US)

(72) Inventor: William S. Gibbons, Jr., Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 84 days.

(21) Appl. No.: 14/200,994

(22) Filed: Mar. 7, 2014

(65) Prior Publication Data
US 2014/0257460 A1 Sep. 11, 2014

Related U.S. Application Data

(60) Provisional application No. 61/776,240, filed on Mar. 11, 2013.

(51) Int. Cl.
A61F 2/06 (2013.01)
A61F 2/966 (2013.01)
A61F 2/82 (2013.01)

(52) U.S. Cl.
CPC . *A61F 2/966* (2013.01); *A61F 2/82* (2013.01); *A61F 2230/0091* (2013.01)

(58) Field of Classification Search
CPC ... A61F 2/966; A61F 2/82; A61F 2230/0091; A61F 2/95; A61F 2/962; A61F 2002/9505; A61F 2002/9517; A61F 2002/9522; A61M 25/0662; A61M 25/005; A61M 2025/0681; A61M 2025/09083; A61M 25/0012; A61M 25/0045; A61M 25/0051; A61M 25/0052; A61M 25/0053; A61M 25/0054; A61M 2025/0046; A61M 2025/0047; A61M 2025/0059; A61M 2025/0062; A61M 2025/0194; A61M 2025/0197; A61M 2025/09066; A61M 2025/09075; A61M 2025/0913; A61M 2025/09133; A61M 2025/091; A61M 2025/0915
USPC .......................................................... 623/1.11
See application file for complete search history.

(56) References Cited

U.S. PATENT DOCUMENTS

| 3,973,556 | A | * | 8/1976 | Fleischhacker et al. ...... 600/585 |
| 4,382,445 | A | | 5/1983 | Sommers |
| 5,460,608 | A | | 10/1995 | Lodin et al. |
| 5,662,622 | A | | 9/1997 | Gore et al. |
| 5,662,675 | A | * | 9/1997 | Polanskyj Stockert et al. ............................. 606/194 |
| 5,863,366 | A | * | 1/1999 | Snow ............................. 156/143 |
| 6,152,912 | A | * | 11/2000 | Jansen et al. ................... 604/526 |
| 6,520,983 | B1 | * | 2/2003 | Colgan et al. ................. 623/1.11 |
| 6,533,770 | B1 | * | 3/2003 | Lepulu et al. ................. 604/524 |
| 6,669,886 | B1 | * | 12/2003 | Willard .................... 264/171.14 |

(Continued)

FOREIGN PATENT DOCUMENTS

EP  0 747 022 A1  12/1996

*Primary Examiner* — Katrina Stransky
(74) *Attorney, Agent, or Firm* — Brinks Gilson & Lione

(57) ABSTRACT

A delivery system for a self-expanding medical device is provided. The delivery system includes an outer sheath that radially restrains the medical device. An inner catheter is disposed within the outer sheath. The inner catheter is a composite structure with an inner layer adhered to the inner diameter of a closed coil wire. The inner catheter has a wave-like pattern along the outer surface that is exposed to the inner surface of the outer sheath.

20 Claims, 3 Drawing Sheets

(56) References Cited

U.S. PATENT DOCUMENTS

| | | | |
|---|---|---|---|
| 7,117,703 B2* | 10/2006 | Kato et al. .................... 72/135 |
| 7,887,529 B2 | 2/2011 | Eder |
| 7,905,877 B1* | 3/2011 | Jimenez et al. ............... 604/525 |
| 7,955,370 B2 | 6/2011 | Gunderson |
| 2001/0010247 A1* | 8/2001 | Snow ........................ 156/171 |
| 2001/0027310 A1* | 10/2001 | Parisi et al. .................. 604/524 |
| 2001/0041881 A1* | 11/2001 | Sarge et al. .................. 604/525 |
| 2001/0044633 A1* | 11/2001 | Klint ............................ 606/200 |
| 2002/0032408 A1* | 3/2002 | Parker et al. ............. 604/103.09 |
| 2002/0151823 A1* | 10/2002 | Miyata et al. ................ 600/585 |
| 2003/0023190 A1* | 1/2003 | Cox ............................... 600/585 |
| 2004/0002727 A1* | 1/2004 | Hwang et al. ................. 606/194 |
| 2004/0002728 A1* | 1/2004 | Speck et al. .................. 606/194 |
| 2004/0082879 A1* | 4/2004 | Klint ............................ 600/585 |
| 2004/0249277 A1* | 12/2004 | Kato et al. .................... 600/434 |
| 2005/0021002 A1* | 1/2005 | Deckman et al. ............. 604/527 |
| 2005/0054952 A1* | 3/2005 | Eskuri et al. ................. 600/585 |
| 2005/0234427 A1* | 10/2005 | Eder ............................. 604/526 |
| 2006/0015168 A1* | 1/2006 | Gunderson ................. 623/1.11 |
| 2006/0030835 A1* | 2/2006 | Sherman et al. ............. 604/526 |
| 2006/0074477 A1 | 4/2006 | Berthiaume et al. |
| 2006/0095110 A1* | 5/2006 | Moberg et al. ............... 623/1.11 |
| 2006/0259011 A1* | 11/2006 | Kubo et al. .................... 604/526 |
| 2006/0265047 A1* | 11/2006 | Dorn ............................ 623/1.12 |
| 2007/0032744 A1* | 2/2007 | Lupton ......................... 600/585 |
| 2007/0060996 A1* | 3/2007 | Goodin et al. ............... 623/1.11 |
| 2007/0100285 A1* | 5/2007 | Griffin et al. ............. 604/164.11 |
| 2007/0191925 A1 | 8/2007 | Dorn |
| 2007/0250040 A1* | 10/2007 | Provost et al. ................ 604/525 |
| 2008/0009831 A1* | 1/2008 | Griffin ........................ 604/531 |
| 2009/0171300 A1* | 7/2009 | Parker et al. .................. 604/264 |
| 2010/0036363 A1 | 2/2010 | Watanabe et al. |
| 2010/0049168 A1* | 2/2010 | Parker et al. ................. 604/527 |
| 2010/0057051 A1* | 3/2010 | Howat et al. ................. 604/526 |
| 2010/0268243 A1* | 10/2010 | Parker .......................... 606/108 |
| 2011/0190865 A1* | 8/2011 | McHugo et al. ............. 623/1.11 |
| 2011/0202128 A1* | 8/2011 | Duffy .......................... 623/2.11 |
| 2011/0264057 A1* | 10/2011 | Eversull et al. ............... 604/265 |
| 2012/0059448 A1* | 3/2012 | Parker et al. ................. 623/1.11 |
| 2012/0059449 A1* | 3/2012 | Dorn et al. .................... 623/1.12 |
| 2012/0101562 A1* | 4/2012 | Gunderson et al. ........... 623/1.12 |
| 2012/0123329 A1* | 5/2012 | Kato ........................... 604/96.01 |
| 2013/0079746 A1* | 3/2013 | Fischell et al. ............... 604/506 |
| 2013/0296915 A1* | 11/2013 | Bodewadt ..................... 606/200 |
| 2014/0200648 A1* | 7/2014 | Newell et al. ................ 623/1.11 |
| 2014/0236279 A1* | 8/2014 | Dillon et al. .................. 623/1.12 |

\* cited by examiner

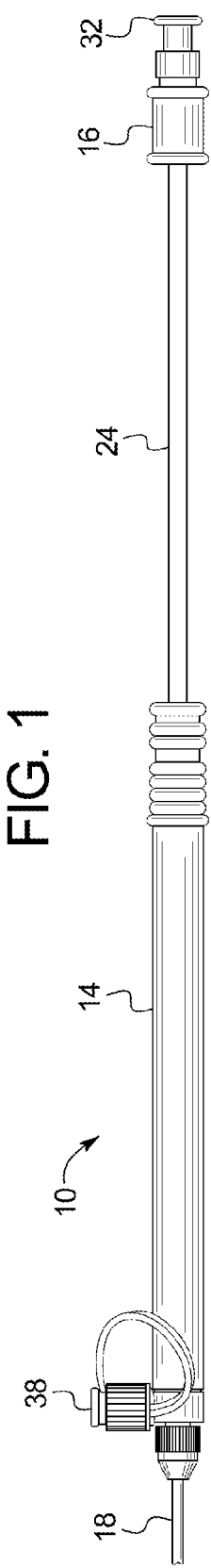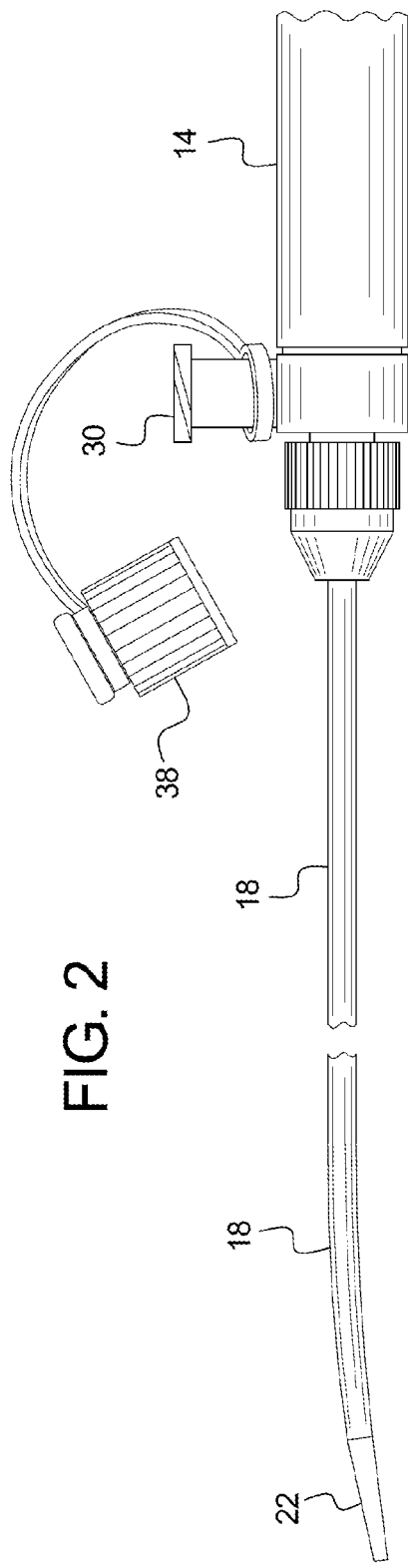
FIG. 1
FIG. 2

INNER CATHETER FOR A SELF-EXPANDING MEDICAL DEVICE DELIVERY SYSTEM WITH A CLOSED COIL WIRE

This application claims priority to U.S. Provisional Application No. 61/776,240, filed Mar. 11, 2013, which is hereby incorporated by reference herein.

BACKGROUND

The present invention relates generally to medical devices and more particularly to delivery systems for medical devices.

Intraluminal medical devices are used by physicians to treat numerous conditions using minimally invasive procedures. Examples of intraluminal medical devices include stents, stent-grafts, filters, valves, etc. One type of intraluminal medical device that has become especially common is self-expanding stents. Typically, self-expanding medical devices, including stents, are made from an elastic structure that may be compressed into a low profile state that can be passed through vessels in a patient with minimal trauma. Once at the desired treatment site, the self-expanding medical device is released and self-expands like a spring until it contacts a tissue wall which prevents further expansion. Common materials that are used in self-expanding medical devices include nitinol and stainless steel, although other materials are also possible.

Self-expanding stents are used to treat various organs, such as the vascular system, colon, biliary tract, urinary tract, esophagus, trachea and the like. For example, stents are commonly used to treat blockages, occlusions, narrowing ailments and other similar problems that restrict flow through a passageway. One area where stents are commonly used for treatment involves implanting an endovascular stent into the vascular system in order to improve or maintain blood flow through narrowed arteries. However, stents are also used in other treatments as well, such as the treatment of aneurysms. Stents have been shown to be useful in treating various vessels throughout the vascular system, including both coronary vessels and peripheral vessels (e.g., carotid, brachial, renal, iliac and femoral). In addition, stents have been used in other body vessels as well, such as the digestive tract.

One type of delivery system for intraluminal medical devices includes an inner catheter and an outer sheath attached to a handle arrangement. One portion of the handle is typically connected to the inner catheter and another portion of the handle is typically connected to the outer sheath. The inner catheter extends coaxially through the outer sheath, and the two portions of the handle are arranged to longitudinally pull the outer sheath relative to the inner catheter. Thus, when the distal end of the delivery system is positioned within the patient's body at the intended treatment site, the physician actuates the handle outside the patient's body by moving the two portions relative to each other so that the outer sheath is withdrawn over the medical device and inner catheter. In the case of self-expanding medical devices, like stents, the outer sheath also serves to radially restrain the device in the compressed state until the outer sheath is withdrawn. As the outer sheath is withdrawn, the medical device is released in the body at the treatment site, and in the case of a self-expanding stent, the stent expands outward away from the inner catheter and presses against the vessel wall. Although the outer sheath is usually withdrawn by pulling the outer sheath proximally relative to the inner catheter, it may also be possible to withdraw the outer sheath by pushing the inner catheter distally relative to the outer sheath. After the medical device has been fully released from the delivery system, the handle may then be pulled by the physician to withdraw the inner catheter and outer sheath from the patient's body, while leaving the medical device implanted in the body.

Precise placement of intraluminal medical devices is a concern in most medical procedures. One problem that can contribute to imprecise placement of intraluminal medical devices is deflection of the delivery system during deployment. This can be a particular problem in the deployment of self-expanding medical devices, like stents, because the medical device presses outward against the inner surface of the outer sheath prior to deployment. When the outer sheath is withdrawn, the outward pressure exerted by the medical device creates friction between the medical device and the outer sheath. Since the medical device is typically prevented from moving proximally with the outer sheath by a stop attached to the inner catheter, the frictional force between the medical device and the outer sheath causes the outer sheath to be in tension and the inner catheter to be in compression. This can cause the inner catheter to contract in length due to the compressive force. In addition, the inner catheter can buckle, or snake, within the outer sheath. Both of these responses can cause the distal end of the inner catheter, and thus the medical device itself, to move proximally from the intended treatment site. Although the contraction and buckling may decrease somewhat as the outer sheath begins to withdraw from the medical device due to the release of some of the frictional force, the distal end of the inner catheter may not completely return to the intended treatment site when the medical device is initially released and implants within the patient's body. Moreover, the stent and/or inner catheter can build up sufficient spring force due to the contraction of the inner catheter and the stent to cause the stent to jump distally once the static friction is released. With medical devices that cause high frictional loads against the outer sheath, like drug coated stents, covered stents and particularly long stents, the initial deflection of the delivery system and subsequent distal movement due to the release of friction can make it difficult for a physician to predict the exact location where the medical device will be released in a patient's body.

Accordingly, the inventor believes it would be desirable to provide an improved delivery system for intraluminal medical devices.

SUMMARY

An improved delivery system is described. The delivery system has an outer sheath, an inner catheter and a self-expanding medical device. The outer sheath radially restrains the medical device in a compressed state within the distal end of the outer sheath. The inner catheter is disposed within the outer sheath and has a stop surface adapted to abut the proximal end of the medical device. The inner catheter has an inner layer adhered to the inside surface of the inner catheter and a wave-like pattern along the outer surface exposed to the inner surface of the outer sheath. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which:

FIG. 1 is a side view of a delivery system;

FIG. 2 is an enlarged side view of the delivery system, showing the distal end of the delivery system;

DETAILED DESCRIPTION

Figure 3:
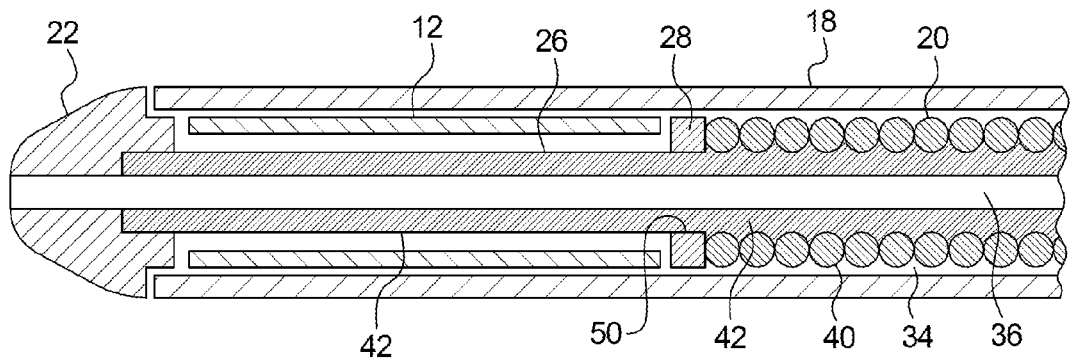
FIG. 3 is a cross-sectional view of the distal end of the delivery system.

Referring now to the figures, and particularly to FIGS. 1-2, a delivery system 10 for a medical device 12 is shown. As shown in FIG. 1, the delivery system 10 includes first and second handle members 14, 16. The first handle member 14 is attached to an outer sheath 18, and the second handle member 16 is attached to an inner catheter 20 (shown in FIG. 3, and as tip 22 in FIG. 2). As shown in FIG. 1, the second handle 16 may be attached to a metal cannula 24 that extends through the first handle 14. The metal cannula 24 may be attached to the inner catheter 20 within the first handle 14. Although the first handle 14 is shown as a larger housing 14 and the second handle 16 is shown as a smaller knob 16, the design of the first and second handles 14, 16 could be reversed so that the second handle 16 is a larger housing and the first handle 14 is a knob that slides relative to the second handle 16. As explained further below, the first and second handles 14, 16 together form a deployment handle that a physician may manipulate outside a patient's body to deploy the medical device 12 inside a patient's body. However, various other types of deployment handles that provide relative longitudinal movement between the outer sheath 18 and the inner catheter 20 are also possible.

As shown in FIG. 3, a medical device 12, such as a self-expanding stent 12, may be loaded into the distal end of the delivery system 10 between the inner catheter 20 and the outer sheath 18. In the loaded state shown in FIG. 3, the stent is compressed within the distal portion of the outer sheath and exerts an outward force against the outer sheath. The inner catheter 20 may be provided with a recessed area 26 to receive the medical device 12, and the outer sheath 18 may cover the outer region of the medical device 12. The inner catheter 20 may also be provided with a stop 28 adjacent the proximal end of the medical device 12. At the distal end of the medical device 12, the inner catheter 20 may be provided with a tapered tip 22 that extends past the distal end of the outer sheath 18 and is suitable for atraumatically passing through body passageways.

The medical device 12 may be delivered into a cavity of a patient's body by positioning the distal portion of the outer sheath 18 and inner catheter 20 (shown at least partially in FIG. 3) within the patient's body. However, the proximal portion of the outer sheath 18 and inner catheter 20 and the first and second handles 14, 16 (shown at least partially in FIG. 1) remain outside the patient's body. Once the delivery system 10 is positioned so that the medical device 12 is located where it is intended to be implanted, the physician slides the first handle 14 relative to the second handle 16 while retaining the second handle 16 in a stationary position. This causes the outer sheath 18 to slide proximally relative to the inner catheter 20. However, because the proximal end of the stent 12 abuts the stop 28, the stent 12 is prevented from moving proximally with the outer sheath 18. Although a certain amount of friction will occur between the outer surface of the stent 18 and the inner surface of the outer sheath 18, the outer sheath 14 is forced to slide proximally relative to the stent 12. As a result, as the distal end of the outer sheath 18 slides past the stent 12, the stent 12 will self-expand outward toward the patient's vessel wall since the stent 12 is no longer radially restrained by the outer sheath 18.

As shown in FIG. 1, the delivery system 10 may be provided with first and second ports 30, 32. The first port 30 is in fluid communication with a space 34 between the inner catheter 20 and outer sheath 18, while the second port 32 is in fluid communication with a longitudinal lumen 36 extending through the inner catheter 20. As is conventionally understood, the second port 32 and inner catheter lumen 36 may be used with a guidewire passing therethrough to guide the delivery system 10 to the desired treatment site. The first port 30 is typically used to flush air out of the space 34 between the inner catheter 20 and the outer sheath 18, which includes the medical device 12 itself. Typically, a saline solution is used for flushing the system 10. The flushing fluid also serves as a lubricant between the inner catheter 20 and outer sheath 18 and between the medical device 12 and outer sheath 18. As shown in FIG. 2, the first port 30 may be provided with a cap 38 that threads onto the first port 30.

Figure 4:
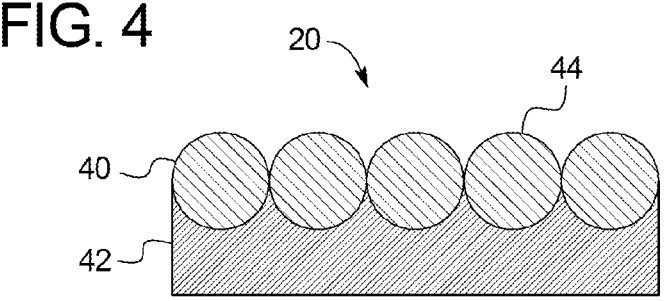
FIG. 4 is an enlarged cross-sectional view of a portion of the inner catheter of the delivery system.
Figure 5:
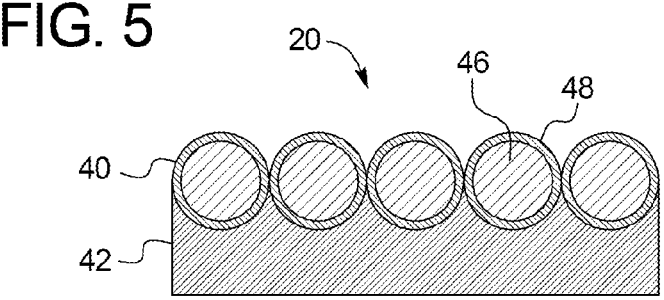
FIG. 5 is an enlarged cross-sectional view of a portion of another embodiment of the inner catheter of the delivery system.
Figure 6:
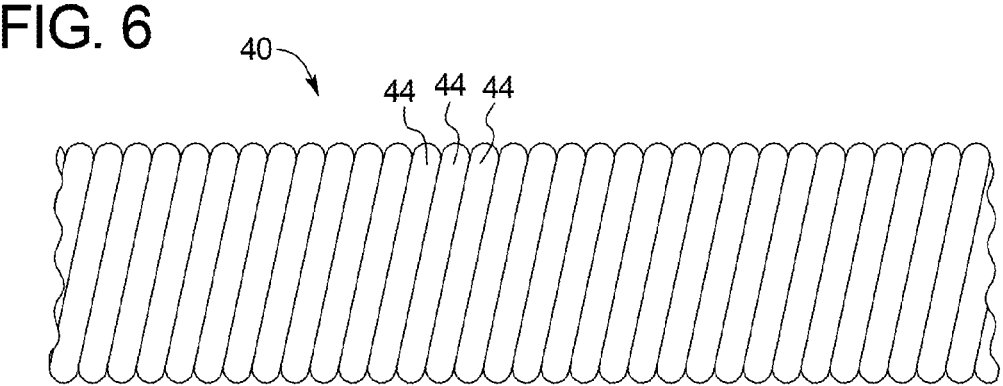
FIG. 6 is a side view of a single wire closed coil.
Figure 7:
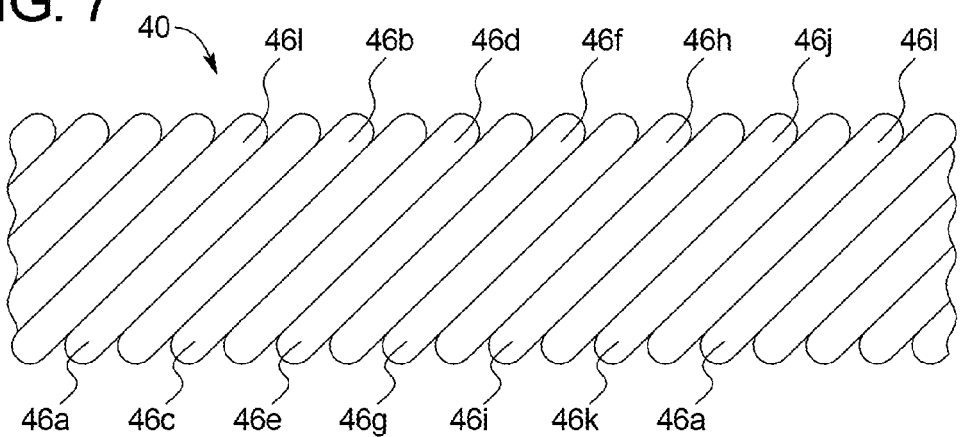
FIG. 7 is a side view of a multiple wire closed coil.

As shown in FIGS. 3-5, the body of the inner catheter 20 is preferably a composite structure with a closed coil wire 40 and a polymer inner layer 42. The closed coil wire 40 is preferably made from one or more metal wires wound in a helical pattern to form a tube 40. For example, one embodiment of the closed coil wire 40 is shown in FIG. 6, in which the closed coil wire 40a is made up of a single wire 44 wound helically around to form a tube 40a. Thus, the wire 44 substantially abuts itself in each winding. Alternatively, as shown in FIG. 7, the closed coil wire 40 may be made up of more than one wire 46a-l. For example, the closed coil wire 40b may have twelve wires 46a-l positioned side-by-side and wound around helically to form a tube 40b. The wound wire tube 40b, similar to FIG. 6, is a closed coil 40 in the sense that each wire winding substantially abuts against adjacent wire windings without substantial gaps between the windings. In FIG. 7, because the closed coil wire 40b is formed of multiple wires 46a-l, each individual wire 46a-l abuts against a different wire 46a-l instead of abutting against itself. As a result, the individual wires 46a-l have a longer pitch than the single wire 44 closed coil 40a of FIG. 6.

As shown in FIGS. 3-5, the polymer inner layer 42 is adhered to the inner diameter of the closed coil wire 40. Preferably, the inner layer 42 is a thermoplastic polymer 42 that is melt bonded to the inner surface of the closed coil wire 40. As shown in FIGS. 4-5, the cross-sections of the wire(s) 44, 46 of the closed coil wire 40 are elliptical, and as a result, the inner and outer surfaces of the closed coil wire 40 each form a wave-like pattern. By contrast, if the wire(s) 44, 46 directly abutted each other like FIGS. 4-5 but the cross-sections of the wire(s) 44, 46 were rectangular, the inner and outer surfaces of the closed coil wire 40 would be smooth instead of having wave-like patterns. Although the cross-sections of the wire(s) 44, 46 are preferably round as shown in FIGS. 4-5, it is possible for the wire(s) 44, 46 to have cross-sections that are non-round, but preferably the cross-sections are not rectangular with corners that substantially abut each other. Because of the cross-sectional shape of the wire(s) 44, 46, the inner portions of the adjacent wire(s) 44, 46 are slightly spaced away from each other even though adjacent wire(s) 44, 46 abut each other at the middle of the cross-sections. In other words, when thought of as a wave-like pattern where the innermost portion of each winding is the top of a wave and the lateral contact between adjacent windings is the bottom of the wave, each wave (or winding) is spaced away from each other between the waves. As a result, when the inner layer 42 is melt bonded to the closed coil wire 40, the polymer 42 penetrates at least partially between adjacent wire windings to better secure the closed coil wire 40 and inner layer 42 together. Although various materials may be used for the inner layer 42, nylon is one preferred material that may be melt bonded to the closed coil wire 40.

As shown in FIG. 4, the inner layer 42 may be adhered directly to the wire(s) 44, 46, which in the case of metal wire(s) 44, 46, would involve adhering the polymer material 42 directly to the metal of the wire(s) 44, 46. Alternatively, as shown in FIG. 5, each of the wire(s) 44, 46 may be individually coated with a lubricious coating 48 like PTFE. Since the lubricious coating 48 conforms to the cross-sections of the wire(s) 44, 46 and does not constitute a distinct layer along the length of the inner catheter 20, the inner and outer surfaces of the closed coil wire 40 retain a wave-like pattern. Thus, in this example, the polymer of the inner layer 42 still penetrates at least partially between adjacent wire windings, but the inner layer 42 is adhered to the lubricious coating 48 instead of directly to the wire(s) 44, 46.

As shown in FIG. 3, the inner catheter 20 preferably has no outer layer adhered to the outer diameter of the closed coil wire 40. Thus, the wave-like pattern along the outer surface of the closed coil wire 40 is exposed to the inner diameter of the outer sheath 18. As noted above, the individual wire(s) 44, 46 of the closed coil wire 40 may be coated as long as the individual wire coating 48 substantially conforms to the wave-like pattern of the wire(s) 44, 46. Thus, coatings 48 around the individual wire(s) 44, 46 are not considered a separate outer layer adhered to the outer diameter of the closed coil wire 40. Preferably, the clearance between the outer diameter of the inner catheter 20 and the inner diameter of the outer sheath 18 is about 0.002" or less per side, when measured from the maximum outer diameter of the wire(s) 44, 46 and the nominal inner diameter of the outer sheath 18. That is, the annular gap between the peaks of the wave-like pattern and the inner surface of the outer sheath 18 is preferably 0.002" or less, and more preferably is about 0.0005" to about 0.0015".

As shown in FIG. 3, the inner layer 42 of the inner catheter 20 may extend past the stop 28 and may be attached to an atraumatic tip 22 distal from the stent 12. For example, the stop 28 may be a metal ring 28, and the inner layer 42 may extend through the lumen 50 of the ring 28 and past the end of the closed coil wire 40. The ring 28 may be melt bonded to the inner layer 42 or otherwise adhered to the inner layer 42. Preferably, the closed coil wire 40 directly abuts the proximal side of the stop ring 28. The inner layer 42 may extend through the lumen of the stent 12 and past the distal end of the stent 12 where it may be adhered to the tip 22. Preferably, the tip 22 extends at least partially distal from the distal end of the outer sheath 18 to form an atraumatic leading end for guiding the delivery system 10 through a patient's body.

Figure 8:
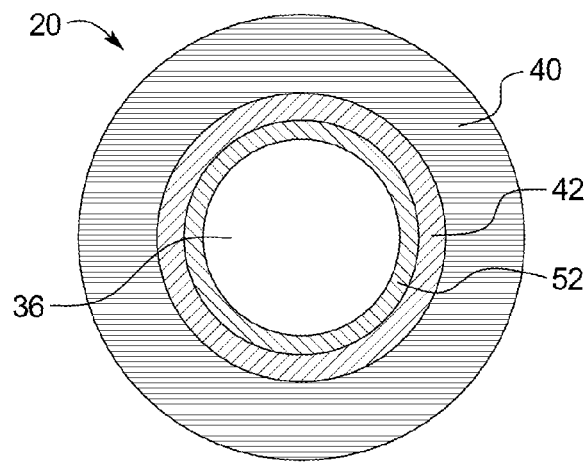
FIG. 8 is a transverse cross-section of another embodiment of the inner catheter.

As shown in FIG. 8, a lubricious layer 52, such as PTFE, may also be adhered to the inner diameter of the inner layer 42. This may be desirable to provide a slick surface exposed to the guidewire lumen 36 to allow the guidewire to smoothly slide through the lumen 36.

The inner catheter 20 may be made by squeezing the inner layer 42 and the closed coil wire 40 together while the inner layer 42 is heated to at least partially melt the inner layer 42. This may be done by supporting the inner layer 42 with a mandrel extending through the lumen of the inner layer 42. The coil 40 may then be wound onto the outer diameter of the inner layer 42 while the inner layer 42 is heated. The closed coil wire 40 could also be wound onto the inner layer 42 while the inner layer 42 is at room temperature so that the closed coil wire 40 exerts inward pressure against the inner layer 42. The mandrel, inner layer 42 and closed coil wire 40 may then be placed in an oven to heat the inner layer 42 and allow the compression of the closed coil wire 40 to squeeze into the inner layer 42. Alternatively, the inner layer 42 may be inserted through the lumen of the closed coil wire 40 and expanded against the inner diameter of the closed coil wire 40 while the inner layer 42 is heated. This may be done by inserting an expandable mandrel through the lumen of the inner layer 42.

After the inner catheter 20 is formed, the inner catheter 20 without an outer layer may be disposed within the outer sheath 18 as shown in FIG. 3. Thus, the wave-like pattern along the outer surface of the closed coil wire 40 is exposed to the inner surface of the outer sheath 18. Preferably, the composite structure of the inner catheter 20 described above extends substantially the entire length from the stop 28 to the deployment handle 14, 16. However, advantages of the delivery system 10 may also be achieved if the composite structure extends about 80% or more of the length between the stop 28 and the deployment handle 14, 16. The stent 12 is also compressed and loaded into the distal end of the outer sheath 18. The stent 12 and inner catheter 20 may be disposed within the outer sheath 18 in whichever order is desired. After the delivery system 10 is assembled, the outer sheath 18 radially restrains the stent 12 to prevent it from expanding until it is deployed, while the inner catheter 20 longitudinally restrains the stent 12 during deployment from moving proximally with the outer sheath 18 as it is withdrawn.

One of the advantages of the delivery system 10 is that the inner catheter 20 may be generally resistant to axial compression while minimizing the tendency of the closed coil wire 40 to buckle during deployment. In particular, unlike conventional reinforcement structures used in various types of catheters, the closed coil wire 40 does not have any substantial longitudinal gaps between adjacent windings as explained above. As a result, compression forces experienced by the inner catheter 20 are transmitted directly through abutting windings since there are no longitudinal gaps between the windings that could compress. However, one problem with closed coil wires 40 like this is that adjacent windings may slide over or under each other when compressive force is applied to the closed coil wire 40. That is, the coil tube 40 may have a tendency to buckle since adjacent wire(s) 44, 46 directly contact each other. However, the inner layer 42 adhered to the inner diameter of the closed coil wire 40 helps to prevent the wire(s) 44, 46 from buckling while still allowing the closed coil wire 40 to bend in use as desired.

Also, because the inner catheter 20 only has an inner layer 42 inside the closed coil wire 40 without having an outer layer on the closed coil wire 40, the closed coil wire 40 may be thicker and the outer diameter may be increased so that it is as close as possible to the inner diameter of the outer sheath 18. Preferably, the annular gap between the inner catheter 20 and the outer sheath 18 is minimized while allowing sufficient space for flushing the delivery system 10. Thus, by increasing the thickness and diameter of the closed coil wire 40, the inner catheter 20 may be strengthened even further to resist compression forces.

In addition, the wave-like pattern of the outer surface of the inner catheter 20 may reduce friction between the inner catheter 20 and outer sheath 18. In contrast to conventional delivery systems where the inner catheter and outer sheath have generally smooth, constant outer and inner diameters, respectively, the inner catheter 20 with a wave-like pattern only contacts the outer sheath 18 at the peaks of the wire(s) 44, 46. Thus, the contact area between the inner catheter 20 and outer sheath 18 is reduced. This may result in lower sliding friction between the inner catheter 20 and outer sheath 18, which may lead to smoother deployments of the stent 12.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A self-expanding medical device delivery system, comprising:
    an outer sheath extending from a proximal portion to a distal portion, said proximal portion being adapted to be attached to a deployment handle and remain outside of a patient's body, said distal portion being adapted to be positioned within said patient's body;
    a self-expanding medical device disposed within said distal portion of said outer sheath, said self-expanding medical device being in a compressed state and exerting an outward force against said outer sheath, wherein said outer sheath restrains said medical device from expanding; and
    an inner catheter disposed within said outer sheath and extending from adjacent a proximal end of said medical device to said deployment handle, said inner catheter comprising a stop surface adapted to abut said proximal end of said medical device;
    wherein said inner catheter comprises a closed coil wire with one or more helically wound wires, said one or more wires each having an elliptical or round cross-section, and an outer surface along a length of said closed coil wire comprising a wave-like pattern defined by said elliptical or round cross-section, a polymer inner layer being adhered to an inner diameter of said closed coil wire, and no outer layer being adhered to an outer diameter of said closed coil wire, said wave-like pattern thereby being exposed to an inner diameter of said outer sheath.

2. The self-expanding medical device delivery system according to claim 1, wherein said medical device is a stent.

3. The self-expanding medical device delivery system according to claim 1, wherein said inner catheter comprises a guidewire lumen extending therethrough.

4. The self-expanding medical device delivery system according to claim 1, further comprising an atraumatic tip attached to a distal end of said inner catheter, said tip extending at least partially distal from a distal end of said outer sheath.

5. The self-expanding medical device delivery system according to claim 1, wherein said closed coil wire comprises a single wound metal wire.

6. The self-expanding medical device delivery system according to claim 1, wherein said closed coil wire comprises multiple wound metal wires.

7. The self-expanding medical device delivery system according to claim 1, wherein said elliptical or round cross-sections of said one or more wires are round.

8. The self-expanding medical device delivery system according to claim 1, wherein said inner catheter comprises a maximum outer diameter defined by said wave-like pattern and said outer sheath comprises a nominal inner diameter, a clearance between said maximum outer diameter and said nominal inner diameter being about 0.002" or less per side.

9. The self-expanding medical device delivery system according to claim 8, wherein said clearance is about 0.0005" to about 0.0015" per side.

10. The self-expanding medical device delivery system according to claim 1, wherein said one or more wires of said closed coil wire are individually coated with a lubricious coating, said lubricious coating conforming to said elliptical or round cross-sections of said one or more wires, and said lubricious coating being exposed to said inner diameter of said outer sheath.

11. The self-expanding medical device delivery system according to claim 10, wherein said lubricious coating comprises PTFE.

12. The self-expanding medical device delivery system according to claim 1, wherein said inner layer is a thermoplastic polymer, said thermoplastic polymer being melt bonded to an inner surface of said closed-coil wire comprising a wave-like pattern defined by said elliptical cross-section of said one or more wires, said polymer thereby penetrating at least partially between adjacent wire windings.

13. The self-expanding medical device delivery system according to claim 12, wherein said inner layer comprises nylon.

14. The self-expanding medical device delivery system according to claim 1, further comprising a lubricious layer adhered to an inner diameter of said inner layer, said lubricous layer being exposed to an inner lumen extending through said inner catheter.

15. The self-expanding medical device delivery system according to claim 14, wherein said lubricious layer comprises PTFE.

16. The self-expanding medical device delivery system according to claim 1, further comprising a metal ring attached to a distal end of said inner catheter, said ring defining said stop surface and comprising an inner lumen extending therethrough, said inner layer extending through said lumen and through said medical device, a tip disposed distal from said medical device being attached to a distal end of said inner layer.

17. The self-expanding medical device delivery system according to claim 1, wherein said medical device is a stent, said inner catheter comprises a guidewire lumen extending therethrough, and said inner layer is a thermoplastic polymer, said thermoplastic polymer being melt bonded to an inner surface of said closed-coil wire comprising a wave-like pattern defined by said elliptical or round cross-section of said one or more wires, said polymer thereby penetrating at least partially between adjacent wire windings.

18. The self-expanding medical device delivery system according to claim 17, wherein said elliptical or round cross-sections of said one or more wires are round, and said inner catheter comprises a maximum outer diameter defined by said wave-like pattern and said outer sheath comprises a nominal inner diameter, a clearance between said maximum outer diameter and said nominal inner diameter being about 0.002" or less per side.

19. The self-expanding medical device delivery system according to claim 18, further comprising an atraumatic tip attached to a distal end of said inner catheter, said tip extending at least partially distal from a distal end of said outer sheath, wherein said one or more wires of said closed coil wire are metal, said one or more wires of said closed coil wire are individually coated with a lubricious coating, said lubricious coating conforming to said elliptical or round cross-sections of said one or more wires, and said lubricious coating being exposed to said inner diameter of said outer sheath, said lubricious coating comprises PTFE, said inner layer comprises nylon, further comprising a lubricious layer adhered to an inner diameter of said inner layer, said lubricous layer being exposed to said guidewire lumen, and wherein said lubricious layer comprises PTFE.

20. A method of manufacturing a self-expanding medical device delivery system, comprising:

disposing an inner layer of a thermoplastic polymer within an inner diameter of a closed coil wire, said closed coil wire comprising one or more helically wound wires, said one or more wires each having an elliptical or round cross-section, and an outer surface along a length of said closed coil wire comprising a wave-like pattern defined by said elliptical or round cross-section;

squeezing said inner layer and said closed coil wire against each other while applying heat to said inner layer, said inner layer at least partially melting, said thermoplastic polymer penetrating at least partially between adjacent wire windings, and said thermoplastic polymer melt bonding to an inner surface of said closed-coil wire comprising a wave-like pattern defined by said elliptical or round cross-section of said one or more wires, said closed coil wire and said inner layer thereby forming an inner catheter;

disposing said inner catheter within an outer sheath, said inner catheter having no outer layer adhered to an outer diameter of said closed coil wire, said wave-like pattern thereby being exposed to an inner diameter of said outer sheath; and compressing and loading a self-expanding medical device into a distal end of said outer sheath, said outer sheath thereby restraining said medical device from expanding, and said inner catheter being disposed adjacent a proximal end of said self-expanding medical device to longitudinally restrain said medical device against moving proximally with said outer sheath during deployment as said outer sheath is withdrawn.

* * * * *